(12) United States Patent
Dillingham et al.

(10) Patent No.: US 8,272,254 B2
(45) Date of Patent: Sep. 25, 2012

(54) DEVICE AND METHOD TO MEASURE WETTING CHARACTERISTICS

(75) Inventors: Raymond Giles Dillingham, Cincinnati, OH (US); Eric Shepherd Oseas, Cincinnati, OH (US); Andrew Davison Gilpin, Cincinnati, OH (US); Francis Charles Ganance, Cincinnati, OH (US)

(73) Assignee: Brighton Technologies Group, Inc, Cincinnati, OH (US)

( * ) Notice: Subject to any disclaimer, the term of this patent is extended or adjusted under 35 U.S.C. 154(b) by 410 days.

(21) Appl. No.: 12/535,435

(22) Filed: Aug. 4, 2009

(65) Prior Publication Data

US 2010/0024529 A1 Feb. 4, 2010

Related U.S. Application Data

(60) Provisional application No. 61/137,821, filed on Aug. 4, 2008.

(51) Int. Cl.
*G01N 13/02* (2006.01)

(52) U.S. Cl. ............... 73/64.52; 73/64.53; 73/73; 73/76

(58) Field of Classification Search ................. 73/64.52, 73/64.53, 73, 76
See application file for complete search history.

(56) References Cited

U.S. PATENT DOCUMENTS

| | | |
|---|---|---|
| 3,483,737 A | 12/1969 | Jennings, Jr. et al. |
| 3,535,043 A | 10/1970 | Hong |
| 3,618,374 A | 11/1971 | Miller |
| 3,696,665 A | 10/1972 | Poppe et al. |
| 4,052,822 A | 10/1977 | Obear |
| 4,196,615 A | 4/1980 | Davis |
| 4,688,938 A | 8/1987 | Demoulin et al. |
| 4,942,760 A | 7/1990 | Almeida |
| 4,970,893 A | 11/1990 | Reid |
| 5,080,484 A | 1/1992 | Schneider et al. |
| 5,115,677 A | 5/1992 | Martin et al. |
| 5,137,352 A | 8/1992 | Blitshteyn et al. |
| 5,143,744 A | 9/1992 | Barth et al. |
| 5,268,733 A | 12/1993 | Wright et al. |
| 5,479,816 A | 1/1996 | Richon et al. |
| 5,583,285 A | 12/1996 | Hahn et al. |
| 5,756,885 A | 5/1998 | Poku et al. |
| 5,838,445 A | 11/1998 | Sandhu et al. |
| 5,861,946 A * | 1/1999 | Hudson et al. ................ 356/150 |
| 6,370,947 B1 | 4/2002 | Casati et al. |
| 6,765,662 B2 | 7/2004 | Casati et al. |
| 6,877,853 B2 | 4/2005 | Kiguchi et al. |
| 7,024,921 B2 | 4/2006 | Sutton |
| 7,155,962 B2 | 1/2007 | Knebel et al. |
| 7,174,775 B2 | 2/2007 | Ishiyama |
| 7,308,822 B2 | 12/2007 | Sutton |

(Continued)

OTHER PUBLICATIONS

Kuhn, A., "Determining Whether a Metal Surface is Really Clean," www.metalfinishing.com (Sep. 2005) pp. 16, 18-21.

(Continued)

*Primary Examiner* — Hezron E Williams
*Assistant Examiner* — Paul West

(57) ABSTRACT

Described herein are a device and method for measuring the wetting characteristics of a liquid on a surface of a material by depositing a volume of liquid on the surface of the material, imparting kinetic energy to the liquid, and obtaining information about the geometry of the volume of the liquid on the surface. The device includes a liquid dispensing component, a kinetic energy imparting component, a position determining component, and a data generating component.

20 Claims, 5 Drawing Sheets

U.S. PATENT DOCUMENTS

| | | | |
|---|---|---|---|
| 7,363,181 | B2 | 4/2008 | Katayama et al. |
| 7,369,253 | B2 | 5/2008 | Zwemer et al. |
| 7,484,403 | B2 * | 2/2009 | Baroni et al. ................. 73/54.37 |
| 7,486,403 | B2 | 2/2009 | Osaka et al. |
| 7,501,154 | B2 | 3/2009 | Senkevich et al. |
| 7,506,552 | B2 | 3/2009 | Hernandez et al. |
| 7,525,545 | B2 | 4/2009 | Brauss |
| 7,543,511 | B2 | 6/2009 | Kimura et al. |
| 7,752,908 | B2 | 7/2010 | Igarashi et al. |
| 7,952,698 | B2 * | 5/2011 | Friedrich et al. ............... 356/138 |
| 2007/0180938 | A1 * | 8/2007 | Baroni et al. .................... 73/866 |
| 2009/0056477 | A1 | 3/2009 | Nishimura et al. |
| 2009/0074966 | A1 | 3/2009 | Henderson et al. |
| 2009/0123639 | A1 | 5/2009 | Denes et al. |
| 2009/0133480 | A1 | 5/2009 | Ivanov et al. |
| 2009/0136654 | A1 | 5/2009 | Xu et al. |
| 2009/0136673 | A1 | 5/2009 | Hiruma |
| 2009/0145640 | A1 | 6/2009 | Toyoda |

OTHER PUBLICATIONS

Miller, R.N., "Rapid Method for Determining the Degree of Cleanliness of Metal Surfaces," Materials Precision and Performance, vol. 12(5) (May 1973) pp. 31-36.

* cited by examiner

DEVICE AND METHOD TO MEASURE WETTING CHARACTERISTICS

CROSS REFERENCE TO RELATED APPLICATIONS

This application claims the benefit of U.S. Provisional Application Ser. No. 61/137,821, filed on Aug. 4, 2008, the disclosure of which is expressly incorporated by reference herein in its entirety.

TECHNICAL FIELD

The invention generally relates to a device and method to measure wetting characteristics of a surface, and more particularly relates to a device and method for depositing a volume of a liquid on a surface and imparting kinetic energy to the volume of liquid and obtaining information about the geometry of the volume of liquid.

BACKGROUND

Surface energy is determined by the chemical composition of the surface and is the result of intermolecular (or in the case of atomic substances, interatomic) attraction. These attractions may be non-specific intermolecular attractions due to the van der Waals-type interactions that exist between all atoms and molecules. These interactions are due to random and transitory fluctuations in electron cloud density that create temporary dipoles which attract each other. Some attractions may also be specific intermolecular attractions between permanent dipoles, between permanent dipoles and induced dipoles, or they may result from electron transfer type interactions such as Lewis type acid-base interactions. Because there are several types of intermolecular interactions responsible for surface tension, there are several components to surface tension. Therefore, surface energy is a multidimensional parameter with terms representing the contributions from each type of intermolecular interaction. To completely determine surface energy requires obtaining as many measurements as there are parameters, typically two or three at a minimum.

Measuring the contact angle of a series of liquid drops on a surface of interest is one frequently used technique to determine surface energy. The contact angle $\theta$ that a liquid forms with a surface is determined by three parameters: the surface energy of the surface ($\gamma s$), the surface energy of the liquid ($\gamma l$), and the interfacial energy between the liquid and the surface ($\gamma sl$), and is described by the Young Equation:

$$\theta = \cos^{-1}\left(\frac{\gamma_s - \gamma_{sl}}{\gamma_l}\right) \quad (1)$$

Contact angles are usually measured using a device known as a contact angle goniometer. A drop of a probe liquid is placed on the surface to be interrogated and allowed to spread equilibrium. The plane of the surface with the drop of liquid is brought into the line of sight of a microscope containing a measuring scale, and a reticle in the microscope is made tangent to the drop profile at the point of contact with the surface. The angle that the reticle makes with the surface is defined as the contact angle. Additional methods have been developed to calculate the contact angle based on the drop shape. These methods depend on obtaining an image of the drop profile.

Contact angle measurements are typically performed in a laboratory setting using cumbersome and delicate devices to take the measurements on small sections of material. These measurements are generally difficult to perform on large planar surfaces found in shop floor settings, particularly ones that are parts of large structures such as automobiles and aircraft. These measurements are also difficult to perform on surfaces that are curved, inclined, or inverted. Unfortunately, many surfaces of interest for contact angle measurements are parts of large, complex structures; and many of these surfaces are also curved, inclined, or inverted. This makes obtaining contact angle measurements on these surfaces very difficult or impossible using current techniques. Also, surfaces that are chemically or physically heterogeneous present additional obstacles to accurately measuring contact angles. The heterogeneities in a surface of a material tend to pin the drop perimeter during spreading, thereby acting as barriers that tend to prevent the drops of liquid from spreading to their equilibrium shape and establishing an equilibrium contact angle. This can introduce significant error into the measurements and result in erroneous values for surface energy.

A need exists for a device and method that can quickly and quantitatively probe the wetting characteristics of the surface of a material or an object. Another need is for a robust device and method that can allow these measurements to be conveniently obtained by semiskilled or unskilled workers in a manufacturing environment. Another need is for a device and method that can perform these measurements on surfaces that are non-planar. Another need is for a device and method that can perform these measurements on surfaces that are non-horizontal, for example inclined or even inverted. One important application for such a device would be to determine if a surface is properly prepared and ready for adhesive bonding or painting. Finally, a need exists for a device and method that can accurately determine the wetting characteristics for surfaces that may be physically or chemically heterogenous.

SUMMARY

Embodiments of the invention address these and other drawbacks and include a device for measuring the wetting characteristics of a liquid on a surface of a material. The device includes a housing, a liquid dispensing component, a kinetic energy imparting component, a position determining component, and a data generating component. The liquid dispensing component is configured to deposit a volume of a liquid on the surface of the material. The kinetic energy imparting component is configured to impart kinetic energy in the form of vibration to the volume of liquid on the surface of the material. The position determining component is configured to convey information about the position of the device relative to the volume of liquid on the surface of the liquid. The data generating component is configured to obtain information about the geometry of the volume of the liquid on the surface of the material.

Also considered is a method for measuring the wetting characteristics of a surface of a material. The method includes depositing a volume of liquid on the surface of the material, imparting kinetic energy to the liquid, and obtaining information about the geometry of the volume of liquid on the surface.

DETAILED DESCRIPTION

When introducing elements of the present invention (e.g., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements. The terms "device" and "method" are intended to mean one or more devices and one or more methods.

Described herein is a device and method that overcomes many of the problems associated with evaluating the wetting characteristics of a surface, measuring contact angles, and obtaining surface energy values. The device and method obviates the need to directly measure a contact angle and overcomes problems associated with equilibration of the shape of the liquid on the surface. Unlike existing instruments, this device can obtain the contact angle on large surfaces that are part of complex structures as commonly found in the shop floor setting, and/or surfaces that are curved, inclined, and/or even inverted. The device and method can also be deployed to probe surfaces that are visually inaccessible to the operator, such as those around a corner or occluded by another part of the structure.

This device deposits a volume of a liquid on the surface of interest. The volume of liquid is small enough that the effect of gravitation on the shape of the volume of liquid is negligible ($\leq 10$ µl for most liquids), and the volume of liquid assumes a spherical profile. For volumes of liquid having a spherical profile, the diameter (d), volume (v) and contact angle are related by the expression:

$$\frac{d^3}{v} = 24\sin^3\theta / (\pi(2 - 3\cos\theta + \cos^3\theta)) \quad (2)$$

Figure 1:
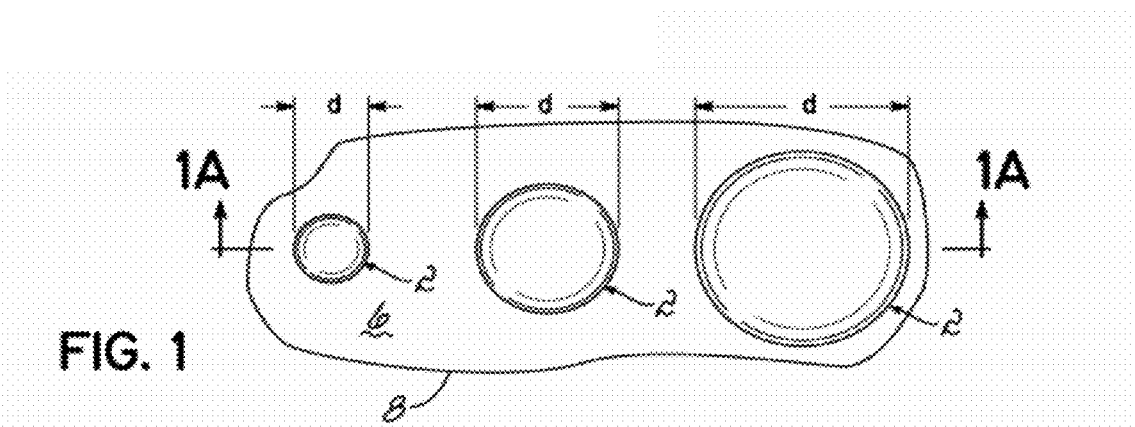
FIG. 1 is a top view of volumes of liquid.
Figure 1A:
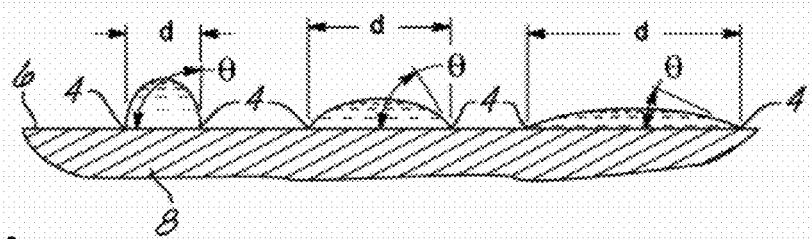
FIG. 1A is a side cross-sectional view of the volumes of liquid in FIG. 1.

As illustrated in FIG. 1, measuring the diameter (d) of the volume of liquid (2) having a known volume allows calculation of contact angle θ formed by the leading edge (4) of the volume of liquid (2) and the surface (6) of the material (8). Thus, in general, as the diameter (d) increases for the volume of liquid (2), contact angle θ decreases. Calculating the contact angle of one or more liquids in this manner allows the surface energy of a material or object to be approximated.

Current techniques for depositing a volume of liquid (2) on a surface using a syringe, or similar device, do not always result in accurate determinations of the contact angle. The true contact angle formed between the volume of liquid (2) and the substrate surface (6) is frequently lower than that measured when such liquid deposition techniques are used because the advancing leading edge (4) of the growing volume of liquid (2) has a tendency to become pinned at surface heterogeneities such as different textures or substrate chemical compositions. One way to overcome this problem is to vibrate the surface of the substrate after depositing the volume of liquid, for example by using acoustic waves. However, this technique is not practical or even possible with many static surfaces found in shop floor settings, such as the surfaces of large structures like automobiles and aircraft. Described herein are a novel device (10) and method for imparting kinetic energy in the form of vibration, shown with wavy lines on FIGS. 2A and 4, to the growing volume of liquid (2). Imparting kinetic energy to the volume of liquid (2) allows for accurate measurement of the wetting characteristics of a liquid on a static surface (6) which can thereby be used to obtain accurate contact angle measurements and/or calculations for the volume of liquid (2) on the surface (6).

The device (10), embodiments of which are shown in FIGS. 2A-7, includes a housing (12), a liquid dispensing component (20), a kinetic energy imparting component (30), position determining component (40) and a data generating component (50). The liquid dispensing component (20), which is also referred to herein as the liquid dispenser (20), is configured to deposit a volume of a liquid (2) on the surface (6) of a substrate material (8). The kinetic energy imparting component (30) is configured to impart kinetic energy in the form of vibration to the volume of liquid (2) on the surface (6) of the material (8). The position determining component (40) is configured to obtain information about the position of the device (10) relative to the volume of liquid (2) on the surface (6). The data generating component (50), also referred to herein as the data generator (50), is configured to obtain information about the geometry of the volume of the liquid (2) on the surface (6) of the material (8). All of these components may be incorporated into a single, handheld device that would be extremely convenient for use in a manufacturing environment on a variety surfaces and structures in a variety of orientations.

In one aspect of the invention, the liquid dispenser (20) and the kinetic energy imparting component (30) are included in the same element, exemplary embodiments of which are shown in FIGS. 2A-3, 5 and 6. The embodiment shown in FIGS. 2A-3, 5 and 6, involves the ballistic deposition of multiple smaller volumes of liquid (60) to the surface (6) of the material (8) to construct the volume of liquid (2). This embodiment includes a nozzle (62) in fluid communication with a liquid reservoir (64). The liquid is pressurized prior to exiting the nozzle (62) and may be pressurized in the reservoir (64), the nozzle (62), or in an intermediate stage, such as in a peristaltic pump (not shown). Pressurization of the reservoir may be accomplished by a piston (66) as shown in FIG. 26 or by other pressurization techniques, such as pumps and gas charging. The nozzle (62) may be electrically actuated between an open state and a closed state such that when in the open state the pressurized liquid is dispensed onto the surface (6) of the material (8) through the nozzle (62), and when in the closed state liquid is not dispensed. This embodiment dispenses pulses of multiple smaller volumes of liquid (60) directed to the same location of the surface (6) of the material (8) to construct the volume of liquid (2). Each successive smaller volume of liquid (60) imparts kinetic energy in the form of vibration, shown as wavy lines, to the growing volume of liquid (2). The kinetic energy prevents pinning of the leading edge (4) of the growing volume of liquid (2) by surface heterogeneities. Volumes of liquid (2) deposited in this manner very rapidly grow to their true equilibrium dimensions.

The smaller volumes of liquid (60) may be on the order of about 10 nl, about 50 nl, about 100 nl, about 200 nl, about 300 nl, or about 400 nl. The smaller volumes (60) are provided in pulses to reach the final volume of liquid (2), which, in one embodiment, may range from between about 0.5 μl to about 10 μl. In another embodiment, the final volume of liquid (2) may range from between about 1 μl to about 5 μl. In another embodiment, the final volume of liquid (2) is about 2 μl. The volume of liquid (2) may be deposited over a relatively short period of time ranging from about 0.01 seconds to about 1.0 seconds. In one embodiment, the volume of liquid (2) is deposited in about 0.5 seconds or less. Other smaller volumes of liquid (60) and final volumes of liquid (2), and deposition times may also be used in the presently described devices and methods.

Figure 3:
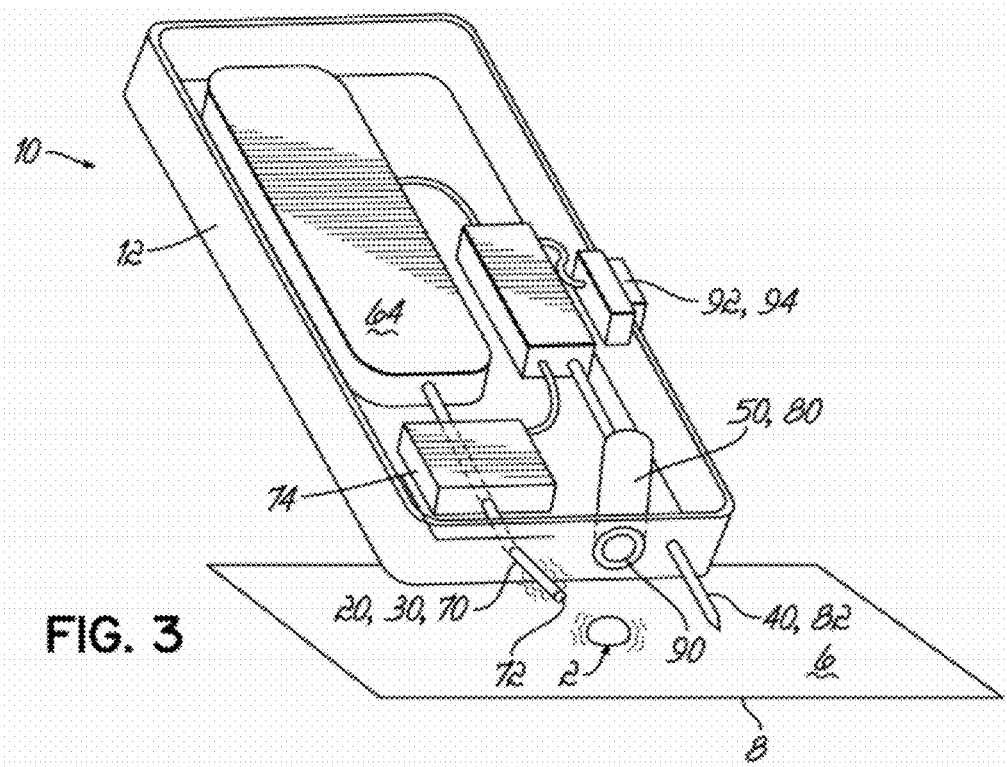
FIG. 3 is a perspective view of another embodiment of the invention.
Figure 4:
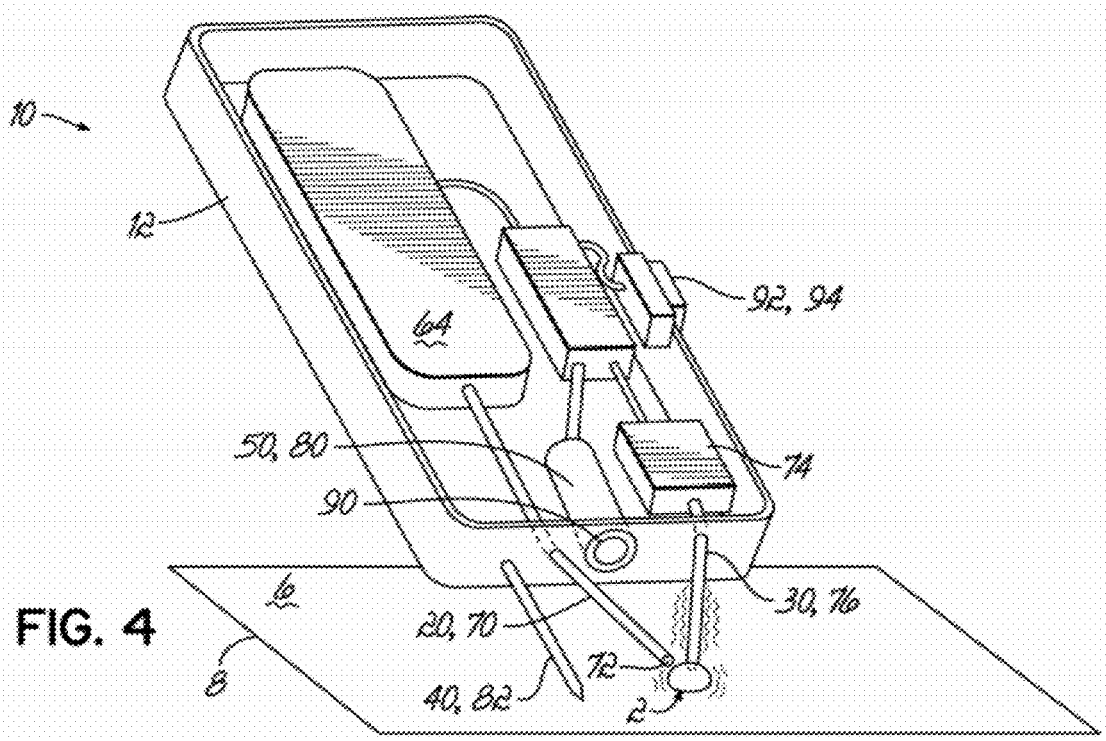
FIG. 4 is a perspective view of another embodiment of the invention.

In another embodiment, shown in FIGS. 3 and 4, the liquid dispensing component (20) is an elongated hollow projection (70) having an opening distal (72) to the housing (12) and a fluid reservoir (64) in fluid communication with the hollow projection (70). Examples of possible elongated hollow projections (70) include syringe needles and pipette tips. The volume of liquid (2) passes from the fluid reservoir (64), through the hollow projection (70), and exits the hollow projection (70) at the distal opening (72) where it is deposited onto the surface (6) of the material (8). The elongated hollow projection (70) may optionally double as the kinetic energy imparting component (30). For example, the hollow projection (70) may be coupled to a device (74) capable of imparting kinetic energy in the form of vibration to the hollow projection (70), which in turn imparts the kinetic energy to the volume of liquid (2). Examples of suitable kinetic energy imparting devices (74) are an electromagnetic transducer, a piezoelectric transducer, an electric motor with an eccentric mass, an acoustical device, and combinations of these devices.

In some embodiments, kinetic energy is imparted to the volume of liquid (2) by a kinetic energy imparting component (30) that is not coupled to the liquid dispensing component (20). For example, as shown in FIG. 4, the kinetic energy imparting component (30) imparts kinetic energy in the form of vibration directly to the volume of liquid (2) deposited on the surface (6). The kinetic energy imparting component (30) in this embodiment may be, for example an acoustic device (not shown) or an elongated projection (76) coupled to a device (74) capable of imparting kinetic energy in the form of vibration to the elongated projection (76), which in turn imparts the kinetic energy to the volume of liquid (2). With this embodiment, kinetic energy may be imparted to the volume of liquid (2) either during or after the deposition of the volume of liquid (2) onto the surface (6) of the material (8).

The position determining component (40) determines the position of the device (10) relative to the volume of liquid (2) on the surface (6) by measuring at least one of the distance of the data generating component (50) from the surface (6) of the material (8) or the angle of the data generating component (50) relative to the surface (6) of the material (8). The position determining component (50) may be as simple as a mechanical probe (82) having a fixed length which maintains a fixed distance between the data gathering component (50) and the volume of liquid (2) on the surface (6). In this embodiment, the mechanical probe (82) contacts the surface (6) of the material (8) to maintain the relative position of data generating component (50). The position determining component (50) may also include a point light source (84), a laser (not shown), and an acoustical measuring device (not shown).

The use of a point light source (84), laser, or acoustical measuring device as the position determining component (40), may allow the device (10) to accurately measure or calculate the contact angles without actually contacting the surface (6) of the material (8). The point light source (84) illuminates an area (86) on the surface (6) of the material. The shape of the illuminated area (86) will be a conic section. The shape of the illuminated area (86) may be analyzed along with the volume of liquid (2) to calculate the distance from the surface (6) and the angle (α) between the plane of the surface (6) and the data gathering component (50). The point light source (84), laser, and acoustical measuring device allow for the construction of a device (10) which merely has to be pointed at the surface (6) from anywhere within a range of distances, such as within a range of about 0.5 inches to about 2 inches, or in a range of about 1 inch to about 1.5 inches. The range of distances over which the device may operate is determined by various factors including, for example, the effective ranges of operation for the liquid dispensing component and/or the data generating component.

Figure 5A:
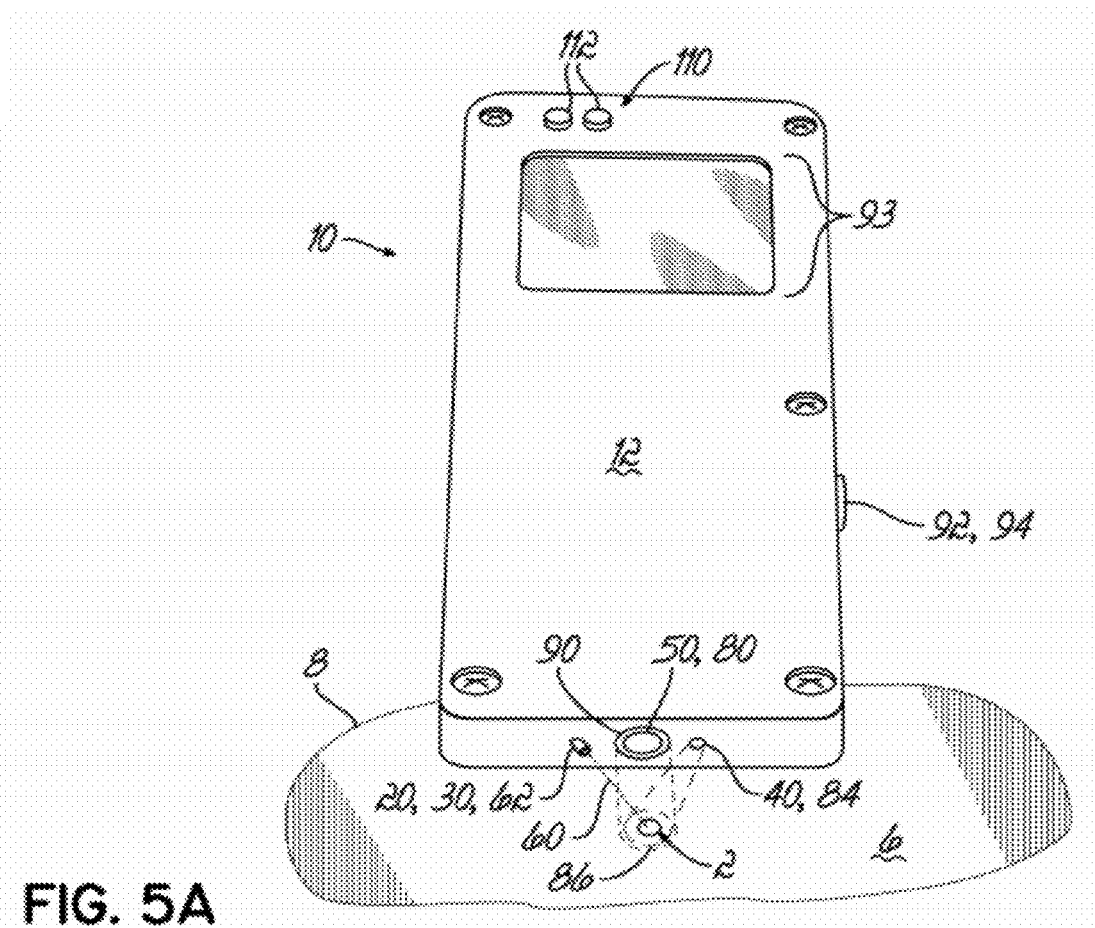
FIG. 5A is a perspective view of another embodiment of the invention.
Figure 5B:
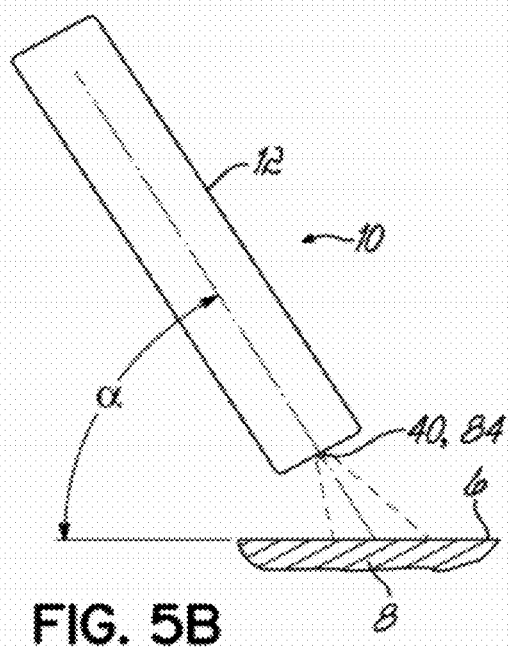
FIG. 5B is a side view of the embodiment of the invention shown in FIG. 5A.

For example, as shown in FIGS. 5A and 5B, a volume of liquid (2) is constructed on a surface (6) by pulsing smaller volumes of liquid (60) from the nozzle (62). Information is almost immediately obtained by the data generating component (50), in this example, a camera (80) records an image of the volume of liquid (2) as well as the illuminated area (86) from the point light source (84). Analysis of the size and shape of the illuminated area (86) allows calculation of the true diameter of the volume of liquid (2) and therefore accurate calculation of the contact angle.

While the mechanical probe (82) and point light source (84) are only shown with some embodiments of the device (10), it is contemplated that any of the liquid dispensing components (20) may function in combination with any of the measuring components (40).

The data generating component (50) is a device capable of obtaining information about the geometry of the volume of liquid (2) on the surface (6) of the material (8). The geometric information includes the shape, the contact angle of the lead edge (4), average contact angle, a diameter (d), the average diameter, and/or the curvature of the volume of liquid (2) on the surface (4) of the material (6). Exemplary data generating components (50) include a camera (80), laser, scanner, and/or an acoustical device. The exemplary data generating component (50) illustrated in the figures is a camera (80). In some embodiments, the data generating component (50) and the position determining component (40) can be included in the same element. For example, a laser or an acoustical device could function as both a data generating component (50) and the position determining component (40).

The device (10) may also include an additional source of illumination (90) such as a light emitting diode, fluorescent, incandescent, strobe light, camera flash, or other suitable source of light for illuminating the volume of liquid (2) on the surface (6) of the material (8). The source of illumination (90) may be incorporated into the housing (12) or may be separate from the housing (12) (not shown). As shown in FIGS. 2A-6, the source of illumination (90) may be a ring of light emitting diodes surrounding a camera (80).

The device is operated by engaging an actuating device (92), such as a button, trigger (not shown), or remote actuator (not shown), that starts the sequence of dispensing the volume of liquid (2) on the surface (6) by the liquid dispensing component (20) and imparting kinetic energy to the volume of liquid (2) via the kinetic energy imparting component (30). The position determining component (40) either insures that the device is the appropriate distance from the surface or determines the distance and/or angle of the data generating component (50) from volume of liquid (2) on the surface (6). The data generating component obtains data about the geometry of the volume of liquid (2). The device may be operated by a single actuating device (92), or, where desired, additional actuating devices or user interfaces (93) could be added to control the device or to input data, such sample information or test parameters. The user interface (93) could include a touch screen (93), a keypad, a toggle, a button, a rollerball, a wheel, a dial, a mouse, etc.

The liquid dispensing component (20), kinetic energy imparting component (30), position determining component (40), and/or the data generating component (50) are optionally coupled to an electronic circuit (94). The electronic circuit (94) may be capable of at least one of sending data to or receiving data from the liquid dispensing component (20), sending data to or receiving data from the kinetic energy imparting component (30), sending data to or receiving data from the data generating component (50), sending data to or receiving data from the position determining component (40), and/or analyzing data received from at least one of the liquid dispensing component (20), kinetic energy imparting component (30), data generating component (50), or position determining component (40).

The electronic circuit may include a microprocessor and may optionally entirely contained within the housing (12). In one embodiment, shown shown in FIG. 7, at least a portion of the circuit is not located in the housing (12). In this embodiment, the circuit in the housing (12) is electronically coupled to the external circuit (not shown) in a secondary housing (96) by, for example, an electrical contact such as found on a docking station (not shown), an electrical cable (98) and/or a wireless connection (100), as illustrated in FIG. 6.

The electronic circuit (94) could also store data collected and generated by the device (10). The stored data could be retrieved from the device (10) by known methods, such as wireless transmission (100) to a remote device (102), storage on removable media (not shown), like a thumb drive or memory chip, and transmission via an electric cable (98) or docking station (not shown). The stored data could have numerous uses such as with quality control and compliance with manufacturing standards and regulations.

Figure 2A:
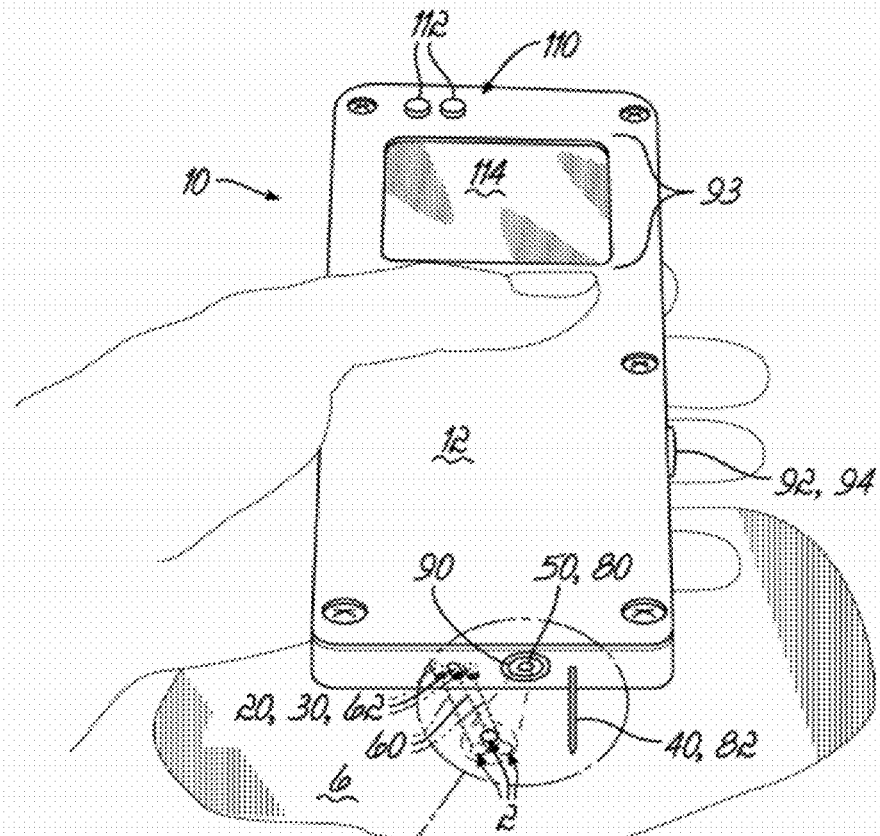
FIG. 2A is a perspective view of an embodiment of the invention.
Figure 2B:
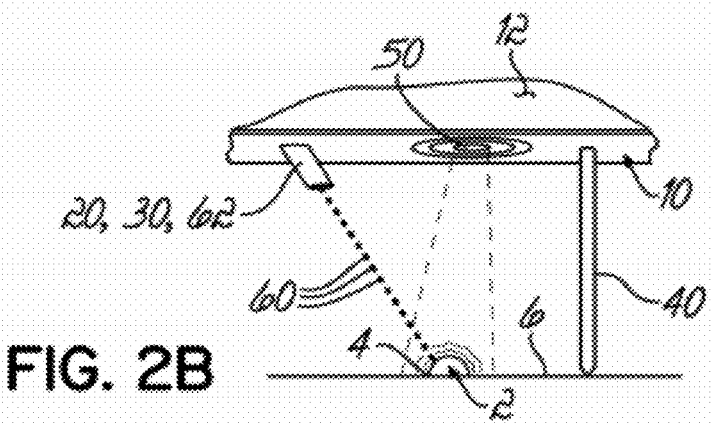
FIG. 2B is an enlarged view of a portion of the embodiment of the invention shown in FIG. 2A.
Figure 6:
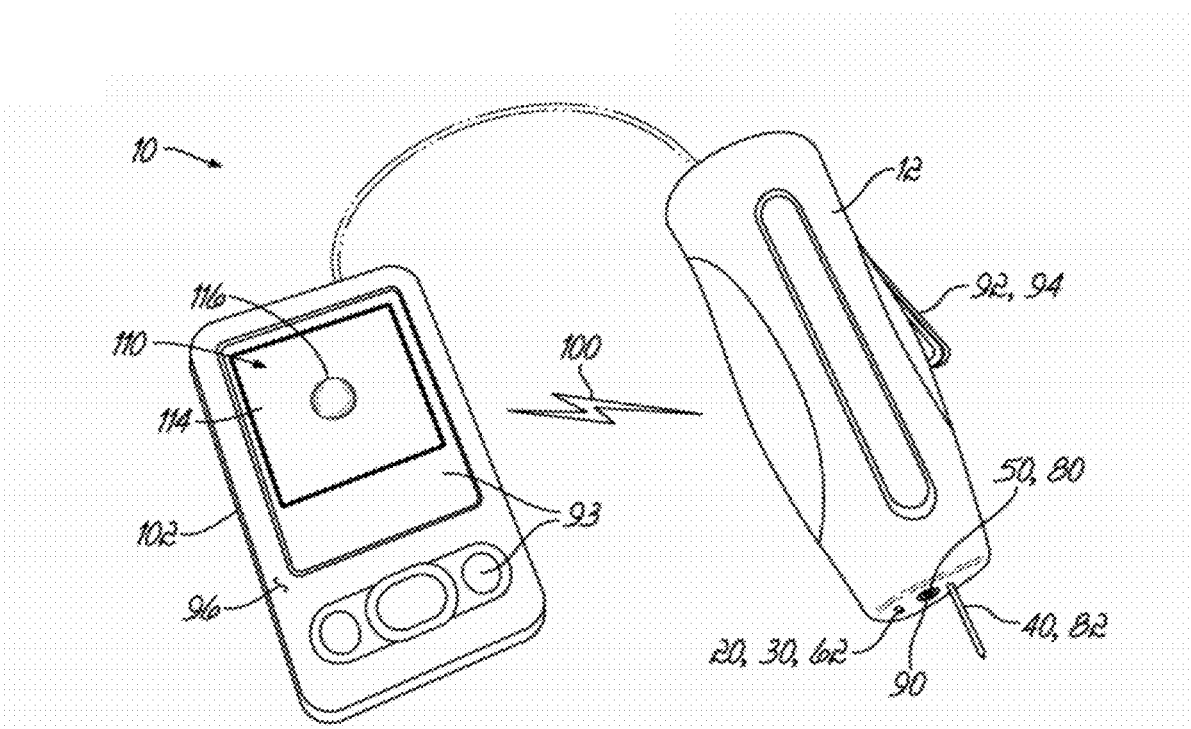
FIG. 6 is a perspective view of another embodiment of the invention.
Figure 7:
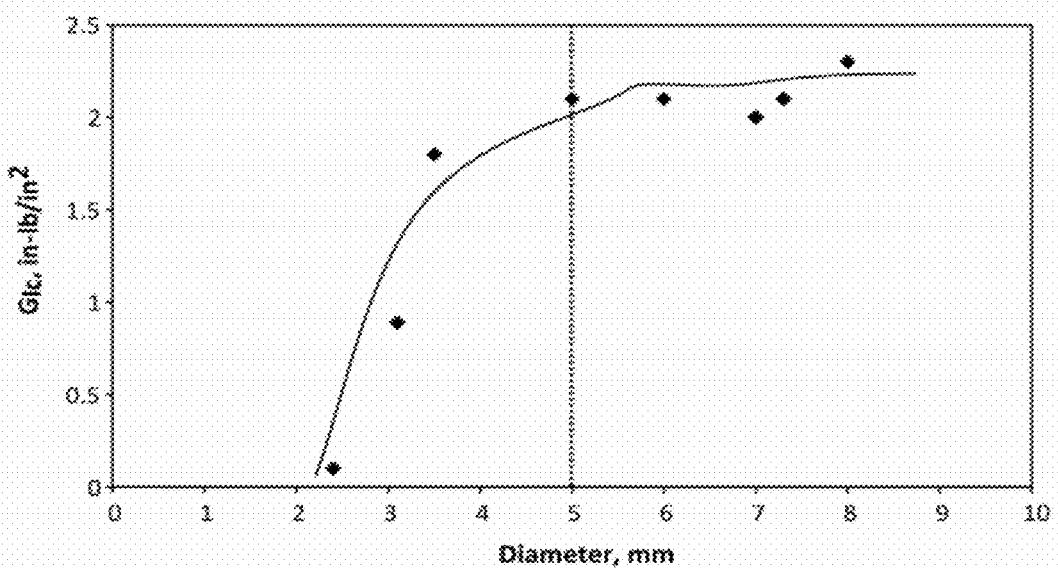
FIG. 7 is a graph of exemplary data generated by an embodiment of the invention.

The device (10) may further include a display (110) coupled to the electronic circuit for displaying information that includes data and/or an image, as shown in FIGS. 2A, 5A, and 6. The display may include a light emitting diode (112) (which includes both individual and screens of light emitting diodes), a liquid crystal display (114), and/or a gauge. The display (110) may be located in or on the housing (12) or, may be located in or on a secondary housing (96) o remote device (102), and coupled to at least a portion of the electronic circuit (94) by at least one of an electrical contact (not shown), electrical cable (98), and a wireless connection (100). The display (110) can convey any information deemed relevant to the use of the device such as the surface energy of the surface, a representation of the volume of the liquid on the surface, an image of the volume of the liquid on the surface (116), a pass indicator, a fail indicator, an error message, a diameter of the volume of the liquid on the surface, an average diameter of the volume of the liquid on the surface, the contact angle formed by the volume of liquid on the surface, the shape of the volume of liquid on the surface, the wetting characteristics of the surface, battery charge, and reservoir volume.

The device (10) may optionally include an auditory signaling device (not shown). The auditory signaling device may be as simple a tone or mixture of tones, or complex as speech. The auditory signaling device may, for example, indicate that the device is in use, that a test was successfully or unsuccessfully completed, a pass or fail indicator, an error, that the device is the correct relative position relative to the surface, battery life, and remaining liquid volume in the reservoir.

Figure 2C:
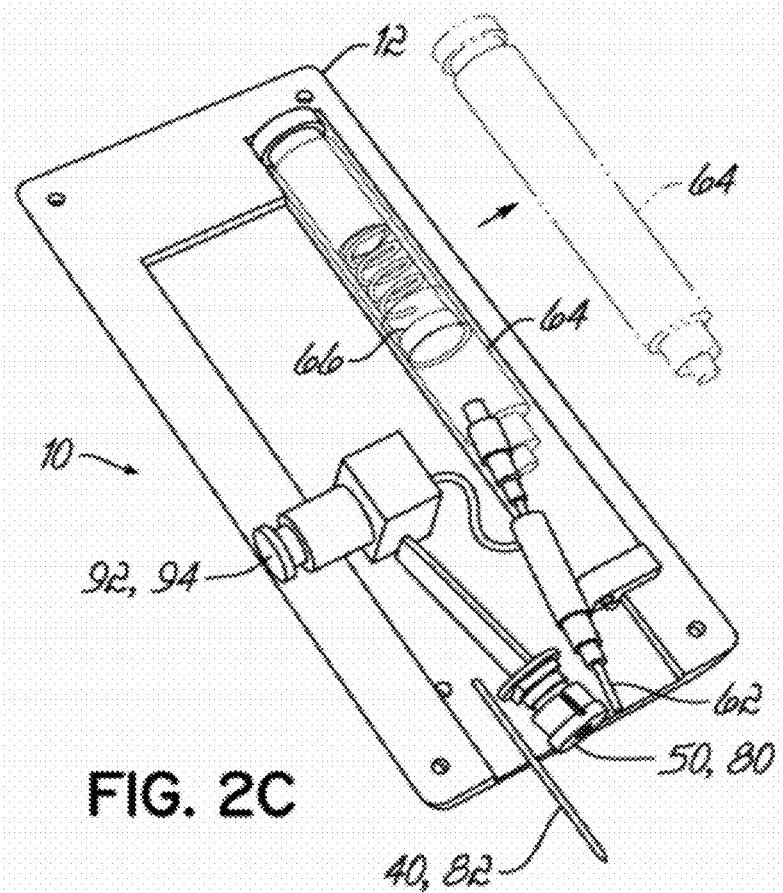
FIG. 2C is an internal perspective view of the embodiment of the invention shown in FIGS. 2A and 2B with the cover removed.

The reservoir 64 may be refilled with liquid or changed by the operator of the device (10). FIG. 2C illustrates the swapping of reservoir 64 with a second reservoir (116).

In use, the wetting characteristics measured by device (10) may predict the quality of adhesion of a paint or adhesive to the surface of a substrate. Adhesion is related to surface energy through the thermodynamic Work of Adhesion. There are several ways to express the relationship between thermodynamic Work of Adhesion and the strength of adhesion. One example is expressed through the following equation:

$$G = W_A \Phi(v,T) \quad (3)$$

Where G=fracture toughness of adhesion
$W_A$=thermodynamic work of adhesion
$\Phi(v,T)$=energy lost to viscoelastic processes during crack propagation
v,T=velocity of crack propagation, temperature Adhesion is therefore directly proportional to the thermodynamic work of adhesion (WA). Thus, it is desirable to be able to predict work of adhesion in order to be able to predict the quality of adhesion between an adhesive or a paint and a substrate.

The work of adhesion may be determined by measuring the contact angle that the adhesive makes with the substrate:

$$W_A = \gamma_l (1 + \cos\theta) \quad (4)$$

However, in general it is very inconvenient to measure the contact angle that an adhesive makes with the surface (6) of a substrate (8). Adhesives are generally too viscous to reach an equilibrium contact angle with a surface (6) in a practical time frame; and low viscosity adhesives generally cure too quickly. Therefore, the work of adhesion is usually calculated using an alternative form of the equation for the work of adhesion that does not require the contact angle of the paint or adhesive to be measured explicitly. One common method for calculation of work of adhesion follows:

$$W_A = 2\sqrt{\gamma_s^d \gamma_l^d} + 2\sqrt{\gamma_s^p \gamma_l^p} \quad (5)$$

Where $\gamma_s^d$=dispersive components of substrate surface energy;
$\gamma_s^p$=polar and dispersive components of substrate surface energy;
$\gamma_l^d$=dispersive components of liquid adhesive surface tension;
$\gamma_l^p$=dispersive components of liquid adhesive surface tension.

While this equation does not require direct measurement of the contact angle of a paint or adhesive, it does require knowledge of the surface energy components of the substrate and the paint or adhesive. The surface energy components of the paint or adhesive can be measured independently and are generally constant. However, the surface energy components of the substrate cannot be assumed. They will vary as a function of the quality of the surface treatment, the storage conditions of the substrate after treatment, and the environment. Controlling the quality of adhesion depends in large part on ensuring that the surface energy of the substrate is repeatable.

The presently described device and method is useful for evaluating work of adhesion either by measuring the contact angle of the paint liquids or adhesive on the substrate (equation 4), or measuring of the contact angles of multiple probe fluids (equation 5), or by measuring the contact angle (or drop diameter) of a single probe liquid, chosen to have surface energy components similar to that of the adhesive or paint. Exemplary liquids that may be used with the device and method described here are deionized water, dimethyl sulfoxide (DMSO), mixtures of formamide with glycol monoethyl ether, mixtures of water and ethanol, and other liquids with desirable wetting characteristics. For example, DMSO is a benign, low viscosity liquid that has surface energy components very similar to those of epoxy adhesives:

TABLE 1

Surface energy components in milli-Joules per square meter.

|  | Epoxy | DMSO |
|---|---|---|
| $\gamma^d$ | 35 | 35 |
| $\gamma^p$ | 5 | 8.7 |

The work of adhesion calculated from DMSO contact angle (or diameter of a small drop) on a surface is an excellent predictor of adhesion. As an example, the data shown in FIG. 7 relate the adhesion of carbon fiber reinforced epoxy laminates that were bonded with a room temperature curing paste epoxy adhesive to the diameter of 3 μl drops of DMSO.

The data shows the general relationship between adhesion (in this case measured as fracture energy) and spreading of a liquid drop as determined by the methods and devices described herein. The X-axis in this figure is presented as the diameter of the volume of liquid, but could easily be present as contact angle or contact area. These particular data were generated with adhesive joints fabricated from carbon fiber reinforced epoxy laminates bonded with a room temperature cure epoxy paste adhesive. The dashed line represents a potential "go/no go" line. In a manufacturing or repair situation, such a line would represent the threshold wetting value: spreading at or above this value would be a signal that the surface was well prepared and ready to bond, while spreading below this value would be indicative of a surface that needed more preparation prior to bonding.

Some research has shown that surface energy $\gamma_s$ is a two-dimensional vector:

$$\gamma_s^T = \gamma_s^P + \gamma_s^d \quad (6)$$

Where $\gamma_s^T$=total surface energy
$\gamma_s^P$=polar component of surface energy
$\gamma_s^d$=dispersion force component of surface energy While other research suggests that surface energy is a three dimensional vector:

$$\gamma_s^T = \gamma_s^a + \gamma_s^b + \gamma_s^{L-W} \quad (7)$$

Where $\gamma_s^T$=total surface energy
$\gamma_s^a$=component of surface energy due to electron accepting character of surface functional groups
$\gamma_s^b$=component of surface energy due to electron donating character of surface functional groups
$\gamma_s^{L-W}$=component of surface energy due to Lifschitz-van der Waals interactions Thus, it may be useful to determine contact angle measurements with two or three liquids in order to evaluate these two- or three component vector quantities and to obtain a more accurate surface energy calculation. Thus, an additional embodiment of the device (10) is capable of depositing either two or three volumes of liquids (2) simultaneously (or in rapid succession) from one or more liquid dispensing components (20), such as nozzles (62), i.e., two or three nozzles (62), imparting kinetic energy to the volumes of liquid (62) and determining the contact angle formed by each volume of liquid (62). The additional volumes of liquid (2) and the additional liquid dispensing components (20), exemplified with nozzles (62), are shown in phantom of FIG. 2A. For example, the device (10) could be outfitted with multiple reservoirs (64) each having a different probe liquid. The additional reservoirs are not shown, but would be configured similar to the reservoirs as previously described. The multiple reservoirs could be in fluid communication with one or more liquid dispensing components (20) to dispense a volume of each liquid (2) on the surface (6) of the material (8). Devices having multiple reservoirs (64) in fluid communication with a single liquid dispensing component (20) would have a cleaning and/or calibration routine for use when switching between liquids. For devices having multiple liquid dispensing components (20), the liquids could be dispensed and analyzed individually or simultaneously. This embodiment would have a component for selecting the desired probe liquid to dispense. The different probe liquids could be used to determine different components of the surface energy for a particular surface type, and/or allow for a single device to be used to evaluate the wetting characteristics/surface energy of with multiple surface types and/or treatments that require interrogation by different probe liquids.

The presently described device and method are useful for determining the wetting characteristic of any surface, and may be particularly useful for surfaces having numerous surface heterogeneities such as varying surface textures. For example, composite surfaces, such as fiberglass composites and carbon fiber materials that have been prepared for adhesive bonding or coating by abrasion or by removal of a peel ply, have a textured surface that corresponds with the direction of the underlying fibers or with the fibers of the peel ply. Volumes of liquid deposited without applying kinetic energy to the liquid tend to assume a shape that corresponds with the direction of the fibers in the underlying ply. The edges of the volume of liquid are pinned in the direction perpendicular to the exposed fibers, preventing the attainment of equilibrium spreading. In contrast, volumes of liquid applied to the same type of surface but using the presently described device and method, i.e., with kinetic energy applied to the liquid, formed spherical drops that could be used to measure the wetting characteristics and to calculate the contact angle.

While device (10) has been described in the exemplary embodiments thus far as being a handheld device, other configurations and uses are contemplated. It is contemplated that the device (10) could be mounted on a movable assembly, such as a robotic arm or carrier system, and operated remotely so that the device may be used to interrogate moving surfaces. For example, device (10) could be used to provide control feedback for continuous treatment processes. Continuous treatment of webs of material, such as polymer for printing purposes or metals such as steel for painting purposes, is made inefficient by the difficulty in obtaining real-time feedback of the surface energy of the material during manufacture. Another embodiment of the device would have the liquid dispensing component (20) and the kinetic energy imparting component (30) mounted in one location of the process, with the position determining component (40) and the data generating component (50) mounted remotely downstream. A geometry of the volume of liquid (2) deposited on the moving web would be evaluated downstream, the wetting characteristics determined, and the data used to control the treatment level in realtime. This would allow the treatment level to be adjusted during processing to obtain the most desired treatment level without overtreating or undertreating the material. The liquid dispensing component (30) could be mounted on a movable assembly that reciprocates at a rate commensurate with the linespeed of the process so that there is no relative motion between the material to be treated and the volume of liquid (2) at the moment of impact. Another possible embodiment would be a liquid dispensing component (2) that is inclined in relation to the plane of the web such that the horizontal velocity of the volume of liquid (2) or, if using ballistic deposition, the smaller volumes of liquid (60) at the time of impact is equal to that of the web.

Although a limited number of embodiments have been described in detail above, those skilled in the art will readily appreciate that many modifications are possible in the embodiments without materially departing from the novel teachings and advantages of this invention. The various features disclosed herein may be used alone or in any desired combination. Accordingly, all such modifications are intended to be included within the scope of this invention. For example, while the detailed description describes devices having one position determining component (50) per device (10), it is fully contemplated that combinations of more than one position determining device (50) may be incorporated into an embodiment of device (10). For example, device (10) could utilize a combination of a mechanical probe (82) and a point light source (84), or two mechanical probes (82), or any combination and number of position determining components (50) as desired.

What is claimed:

1. A device for measuring the wetting characteristics of a liquid on a surface of a material comprising:
    a housing, a liquid dispensing component, a kinetic energy imparting component, a position determining component, and a data generating component,
    wherein the liquid dispensing component is configured to deposit a volume of a liquid on the surface of the material;
    wherein the kinetic energy imparting component is configured to impart kinetic energy in the form of vibration to the volume of liquid on the surface of the material;
    wherein the position determining component is configured to convey information about the position of the device relative to the volume of liquid on the surface of the liquid and to convey information about at least one of the distance of the data generating component from the surface and the angle of the data generating component relative to the surface; and
    wherein the data generating component is configured to obtain information about the geometry of the volume of the liquid on the surface of the material.

2. The device of claim 1 wherein the liquid dispensing component and the kinetic energy imparting component are included in the same element.

3. The device of claim 2 wherein the liquid dispensing component is configured to deposit the volume of liquid on the surface of the material and impart kinetic energy to the volume of liquid by depositing multiple smaller volumes of liquid to the surface of the material to construct the volume of liquid.

4. The device of claim 1 wherein the liquid dispensing component includes a nozzle and liquid reservoir in fluid communication with the nozzle.

5. The device of claim 4 wherein the nozzle is electrically actuated between an open state and a closed state and the liquid is pressurized.

6. The device of claim 1 wherein the liquid dispensing component includes an elongated hollow projection having an opening distal to the device and a fluid reservoir in fluid communication with the projection.

7. The device of claim 6 wherein the hollow projection is coupled to a device capable of imparting kinetic energy in the form of vibration to the hollow projection.

8. The device of claim 1 wherein the kinetic energy imparting component is at least one of an acoustic device and an elongated projection coupled to a device capable of imparting kinetic energy in the form of vibration to the projection.

9. The device of claim 1 wherein the data generating component is selected from the group consisting of a camera, a laser, a scanner, an acoustical device, and combinations thereof.

10. The device of claim 1 wherein the position determining component conveys information about at least one of the distance of the data generating component from the surface and the angle of the data generating component relative to the surface.

11. The device of claim 10 wherein the position determining component is selected from the group consisting of a mechanical probe, a point light source, a laser, an acoustical device, and combinations thereof.

12. The device of claim 1 wherein at least one of the liquid dispensing component, the position determining component, and the data generating component is electronically coupled to an electronic circuit.

13. The device of claim 12 wherein the electronic circuit is capable of at least one of sending data to or receiving data from the liquid dispensing component, sending data to or receiving data from the data generating component, sending data to or receiving data from the position determining component, and analyzing data received from at least one of the liquid dispensing component, the data generating component, and the position determining component.

14. The device of claim 12 wherein at least a portion of the electronic circuit is not located in the housing and is coupled to the electronic circuit in the housing by at least one of an electrical contact, an electrical cable and a wireless connection.

15. The device of claim 12 further comprising a display electronically coupled to the electronic circuit, wherein the display is capable of conveying information including at least one of data and an image.

16. A method for measuring the wetting characteristics of a surface of a material comprising:
    depositing a volume of liquid on the surface of the material;
    imparting kinetic energy to the volume of liquid in a manner that allows for free vibration of the liquid; wherein the vibration is of sufficient amplitude to facilitate attainment of an equilibrium contact angle between the liquid and the surface; and
    wherein the depositing of liquid on the surface of the material and the imparting kinetic energy to the volume of liquid is by the deposition of the volume of liquid to the surface of the material to form the volume of liquid; and
    obtaining information about the geometry of the volume of the liquid on the surface such that the geometry of the liquid formed after an equilibrium has been achieved can be determined.

17. The method of claim 16 further comprising pressurizing a fluid in a reservoir coupled to a nozzle, electrically actuating the nozzle between an open state and a closed state, allowing fluid to pass through the nozzle when in the open state thereby depositing the volume of fluid on the surface of the material and imparting kinetic energy to the liquid.

18. The method of claim 16 wherein the kinetic energy is imparted to the volume of liquid by the deposition of multiple smaller volumes of liquid to the surface of the material to form the volume of liquid.

19. A method for measuring the wetting characteristics of a surface of a material comprising:
   depositing a volume of liquid on the surface of the material;
   imparting kinetic energy to the volume of liquid in a manner that allows for free vibration of the liquid; wherein the vibration is of sufficient amplitude to facilitate attainment of an equilibrium contact angle between the liquid and the surface; and wherein the kinetic energy is imparted by at least one of an acoustic device and an elongated projection coupled to a device capable of imparting kinetic energy in the form of vibration to the projection; and
   obtaining information about the geometry of the volume of the liquid on the surface such that the geometry of the liquid formed can be determined after an equilibrium contact angle has been achieved.

20. The method of claim 19 wherein the volume of liquid is deposited by an elongated hollow projection.

* * * * *